(12) United States Patent
Wang et al.

(10) Patent No.: US 10,451,613 B1
(45) Date of Patent: Oct. 22, 2019

(54) RAPID DIAGNOSTIC TEST DEVICE AND SAMPLING METHOD USING DRIVEN FLOW TECHNOLOGY

(71) Applicant: DNT SCIENTIFIC RESEARCH, LLC, San Diego, CA (US)

(72) Inventors: Naishu Wang, Poway, CA (US); Michael Chang Chien, Cerritos, CA (US)

(73) Assignee: DNT SCIENTIFIC RESEARCH, LLC, San Diego, CA (US)

( * ) Notice: Subject to any disclaimer, the term of this patent is extended or adjusted under 35 U.S.C. 154(b) by 0 days.

(21) Appl. No.: 16/185,455

(22) Filed: Nov. 9, 2018

(51) Int. Cl.
  *G01N 33/53* (2006.01)
  *G01N 1/02* (2006.01)
  *G01N 33/543* (2006.01)

(52) U.S. Cl.
  CPC ........... *G01N 33/5302* (2013.01); *G01N 1/02* (2013.01); *G01N 33/54386* (2013.01); *G01N 2001/028* (2013.01)

(58) Field of Classification Search
  CPC ................. G01N 33/5302; G01N 1/02; G01N 33/54386; G01N 2001/028
  USPC ........................................................ 422/424
  See application file for complete search history.

(56) References Cited

U.S. PATENT DOCUMENTS

| | | |
|---|---|---|
| 4,299,916 A | 11/1981 | Litman et al. |
| 4,366,241 A | 12/1982 | Tom et al. |
| 5,352,410 A | 10/1994 | Hansen et al. |
| 5,403,551 A | 4/1995 | Galloway et al. |
| 5,656,503 A | 8/1997 | May et al. |
| 6,140,136 A | 10/2000 | Lee |
| 6,372,514 B1 | 4/2002 | Lee |
| 6,379,620 B1 | 4/2002 | Tydings et al. |
| 6,403,383 B1 | 6/2002 | Casterlin et al. |
| 6,730,268 B2 | 5/2004 | Lee et al. |
| 6,805,837 B2 | 10/2004 | Tydings |
| 6,875,185 B2 | 4/2005 | Wong et al. |
| 7,431,882 B2 | 10/2008 | Parker |
| 7,741,103 B2 | 6/2010 | Guirguis |
| D626,249 S | 10/2010 | Wang et al. |
| 7,879,623 B2 * | 2/2011 | Guirguis ............ A61B 10/0051 422/422 |
| 7,981,382 B2 | 7/2011 | Wong et al. |

(Continued)

*Primary Examiner* — Jill A Warden
*Assistant Examiner* — Jacqueline Brazin
(74) *Attorney, Agent, or Firm* — Innovation Capital Law Group, LLP; Vic Lin

(57) ABSTRACT

A progressive compression driven flow cartridge for analyzing liquids is coupled with convenient sampling methods for different applications. A one-step device provides for direct sample collection upon a sample pad annexed to the cartridge. The sample pad can deliver sample to the test strips, while saving a portion of the sample pad for further laboratory confirmation use. If the sample collecting pad is not suitable to collect the sample, such as the case of biological substances inside the human body, such as within the nose or throat, a two-step device can include a long-arm swab applicator and a specialized chamber in which some amount of liquid can dissolve biological substances as specimen. The specimen can then be transferred onto the cartridge, either by application to the sample pad, or into the device through a sample window. Each method provides a qualitative analysis much faster than traditional rapid diagnostic devices.

13 Claims, 6 Drawing Sheets

(56) References Cited

U.S. PATENT DOCUMENTS

| | | |
|---|---|---|
| 8,021,625 B2 | 9/2011 | Wang et al. |
| 8,071,394 B2 | 12/2011 | Wu et al. |
| 8,163,253 B1 | 4/2012 | Hartselle |
| 8,206,661 B2 | 6/2012 | Vallejo et al. |
| 8,394,626 B2 | 3/2013 | Ramsey et al. |
| 8,889,424 B2 | 11/2014 | Ehrenkranz et al. |
| 8,916,390 B2 | 12/2014 | Ozcan et al. |
| 8,940,527 B2 | 1/2015 | Guirguis |
| 8,992,855 B2 | 3/2015 | Lin |
| 9,377,457 B1 | 6/2016 | Wang et al. |
| 9,414,813 B2 | 8/2016 | Engel et al. |
| 9,535,061 B1 | 1/2017 | Wang et al. |
| 9,632,083 B1 * | 4/2017 | Wang ............... G01N 33/54366 |
| 9,702,872 B1 * | 7/2017 | Wang ................... B01L 3/5023 |
| 2004/0152206 A1 | 8/2004 | Davis et al. |
| 2005/0147537 A1 * | 7/2005 | Sangha ................ A61B 90/96 422/550 |
| 2005/0163660 A1 | 7/2005 | Wang |
| 2006/0029517 A1 | 2/2006 | Hartselle |
| 2006/0292700 A1 | 12/2006 | Wang et al. |
| 2007/0054414 A1 * | 3/2007 | Burgess-Cassler ......... B01L 3/5023 436/514 |
| 2007/0065339 A1 | 3/2007 | Huff |
| 2007/0259442 A1 | 11/2007 | Gould et al. |
| 2008/0199851 A1 * | 8/2008 | Egan .................... B01L 3/5023 435/5 |
| 2009/0208371 A1 * | 8/2009 | Hannant ............ A61B 10/0045 422/400 |
| 2010/0278692 A1 | 11/2010 | Chen |
| 2012/0301893 A1 * | 11/2012 | Siciliano ............... B01L 3/5023 435/7.1 |
| 2013/0022517 A1 | 1/2013 | Engel et al. |
| 2015/0173742 A1 | 6/2015 | Palese et al. |
| 2015/0203904 A1 | 7/2015 | Hopper |
| 2015/0211987 A1 | 7/2015 | Burg et al. |
| 2016/0025752 A1 | 1/2016 | Santiago et al. |
| 2017/0203040 A1 | 7/2017 | Conlan et al. |

* cited by examiner

RAPID DIAGNOSTIC TEST DEVICE AND SAMPLING METHOD USING DRIVEN FLOW TECHNOLOGY

BACKGROUND OF THE INVENTION

1. Field of the Invention

One or more embodiments of the invention relate generally to apparatus for analyzing liquids, such as body fluids, using labeled molecular affinity binding, such as immunochromatography. More particularly, the invention relates to a progressive compression driven flow cartridge for analyzing liquids, such as some bodily fluids and tracing biological substances, coupled with convenient sampling methods in different applications.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Labeled molecular affinity binding such as immunochromatographic assays have existed for decades and have proven to be an inexpensive way to screen for various conditions such as abused drugs and other conditions such as pregnancy, cancer, or for single or multiple pathogenic conditions such as HIV infection.

In the point-of-care test (POCT) field, immunochromatographic assays are typical conducted using lateral flow strip technology as described in May et al., U.S. Pat. No. 5,656,503 incorporated herein by reference. Unfortunately, although they can be fast, inexpensive, and simple-to-use, depending on the type of condition being detected, these tests provide a typical accuracy of between 75% and 95%, falling short of the 99% or above accuracy generally considered to be necessary for a confirmatory test, and providing no objective measure of a quantitative result, i.e. the concentration of a given drug present in the liquid being tested.

The reasons for the insufficient accuracy in many rapid in vitro diagnostic (IVD) test devices are primarily due to their current lack of overall higher sensitivity and specificity. Different samples may contain chemicals or particles which intrinsically inhibit liquid flow mixed well with reagents or otherwise interfere with one or both of the first and second affinity binding reactions.

Prior devices have attempted to enhance sensitivity or specificity by pretreating various parts of the device with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially in the reaction zones region of the strip. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Or, the manufacturing step of pretreating with the second pretreatment chemical can dislodge some of the first pretreatment chemical.

Further, lot-to-lot variation in the manufacture of many IVD test devices can often lead to ambiguous results, such as false negatives as well as weak false positives, so-called "ghost lines" or "phantom lines". False negatives typically occur when non-specific molecules interfere with the first and/or second affinity binding actions. It has been found that non-analyte molecules can clump together in liquid samples that are not well mixed so that they temporarily prevent access between analytes and binding members. Even temporary interference in past devices can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive result.

Lateral flow devices are useful due to their low cost and ease of use. However, prior lateral flow devices suffer from low accuracy as detailed above. This is especially true for saliva testing because of the low concentrations of analytes present. Current lateral flow strips cannot provide the necessary sensitivity and specificity within the time normally allotted to a typical law enforcement action such as a traffic stop.

The low accuracy can be due to a number of problems unique to lateral flow-type tests. First, there is often uneven movement of the immunoparticles within the nitrocellulose membrane. Smaller, non-analyte molecules mixed together with the larger analyte molecules and compete for sites and often prevent the larger molecules from reacting in the desired fashion.

Therefore, there is a need to improve the accuracy of rapid IVD test devices so that rapid inexpensive easily conducted qualitative immunological testing becomes a reality.

SUMMARY OF THE INVENTION

Embodiments of the present invention provide a device for testing a liquid sample for the concentration of at least one analyte comprising a test cartridge having a base component supporting a test strip, a top component fitting onto the base component, sandwiching the test strip with the base component, a flexible pad disposed between the base component and the top component, the flexible pad positioned at least over a portion of a pad of the test strip when the test strip is disposed in the test cartridge, and a cap slidable over a first end of the test cartridge having the flexible pad disposed therein, the cap including an internal ramp causing the top component to be pressed toward the base component as the cap is slid onto the test cartridge.

In some embodiments, the device further includes a ring surrounding a portion of the base component and the top component, the ring positioned to surround at least a conjugate pad portion of the test strip when the test strip is disposed in the test cartridge.

In some embodiments, the device further includes auxiliary supports extending from the base component, the auxiliary supports positioned to support at least a portion of the test strip when the test strip is disposed in the test cartridge.

In some embodiments, the auxiliary supports include a support positioned below a conjugate pad of the test strip when the test strip is disposed in the test cartridge.

In some embodiments, the test cartridge further includes a reading window formed as an opening or clear window in the top component, the reading window providing visual access a portion of the test strip when the test strip is disposed in the test cartridge.

In some embodiments, the flexible pad extends beyond the first end of the test cartridge.

In some embodiments, the device further includes a snipping knife disposed on the first end of the top component of the test cartridge, the snipping knife configured to cut the flexible pad when the cap is pressed onto the first end of the test cartridge.

In some embodiments, an external cut portion of the flexible pad is retained inside the cap after being cut by the snipping knife.

In some embodiments, the test cartridge further comprises a sample well formed as an opening in the top component for placement of a sample on the pad of the test strip when the test strip is disposed inside the cartridge.

Embodiments of the present invention provide a system for testing a liquid sample for the concentration of at least one analyte comprising one or more test strips, each comprising a pad configured on one end of each of the one or more test strips, and a conjugate pad containing nanoparticle conjugate; and a test cartridge comprising a base component supporting each of the one or more test strips next to each other, a top component fitting onto the base component, sandwiching each of the one or more test strips with the base component, a flexible pad disposed between the base component and the top component, the flexible pad positioned at least over a portion of the test strip, and a cap slidable over a first end of the test cartridge having the flexible pad disposed therein, the cap including an internal ramp causing the top component to be pressed toward the base component as the cap is slid onto the test cartridge.

Embodiments of the present invention also provide an applicator for collecting a sample, comprising a swab attached to a first end of an elongated shaft; a handle attached to a second end of the elongated shaft; male threads formed in a region where the handle meets the elongated shaft; female threads, configured to mate with the male threads, formed on an open end of a swab receiving chamber; a sample releasing region disposed on an end of the chamber, wherein, when the swab is inserted into the chamber, the swab is received in the sample releasing region; a narrowed region extending from the sample releasing region, wherein when the male threads are threaded into the female threads, the swab extends into the narrowed region; and a cap 90 configured to provide a fluid connection from the narrowed region to outside the chamber.

In some embodiments, the sample releasing region includes a sample releasing fluid configured to remove a sample from the swab.

In some embodiments, the male threads and female threads are configured to permit from about 3 to about 4 turns when mated together.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
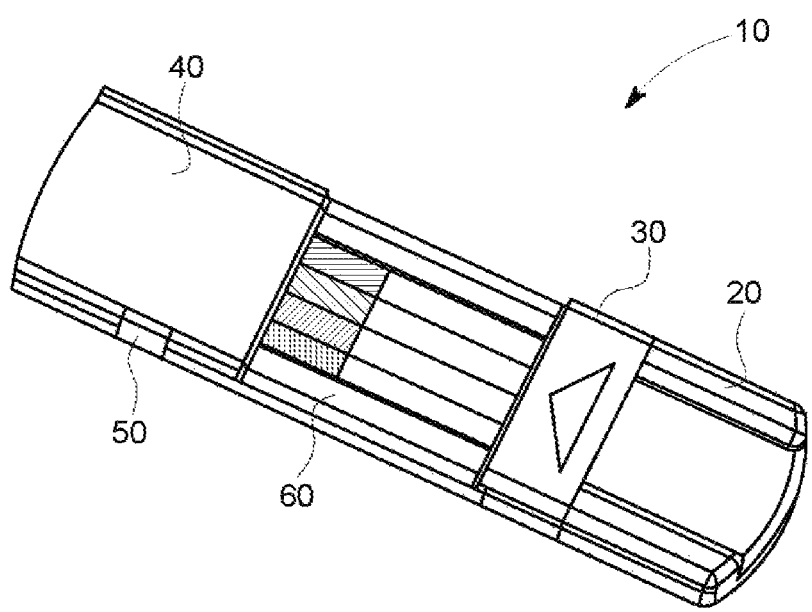
FIG. 1 illustrates a perspective view of a diagnostic test device according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a progressive compression driven flow cartridge for analyzing liquids coupled with convenient sampling methods for different applications. Some liquid uses labeled molecular affinity binding, such as immunochromatography, flowed onto test strips in a cartridge for detecting at least an analyte, such as an antibody or antigen, which may indicate a particular condition, or the presence of a specific drug or virus depending on the test format. A one-step device provides for direct sample collection upon a testing pad annexed to the cartridge. The sample pad can deliver sample to the test strips, while saving a portion of the testing pad for further laboratory confirmation use. If the sample collecting pad is not suitable to collect the sample, such as the case of biological substances inside the human body, such as within the nose or throat, a two-step device can include a long-arm swab applicator and a specialized chamber in which some amount of liquid can dissolve biological substances as specimen. This specimen can then be transferred to the cartridge, either by delivering the specimen to the sample pad extending from the cartridge, or by delivering the specimen directly into a sample window formed in the cartridge. Each method provides a qualitative analysis much faster than traditional rapid diagnostic devices.

Referring to FIG. 1, a driven flow cartridge 10, also referred to as test cartridge 10 or simply, cartridge 10, can include a cap 20 fitting over a sample receiving end of the cartridge 10. A ring 30 may be formed about the cartridge 10 at a position adjacent the cap 20, when the cap 20 is fully inserted onto the end of the cartridge 10. The cartridge 10 may be formed from a top portion 40 and a bottom portion 50 held together as discussed below. Test strips may be disposed within the cartridge 10. While four text strips are shown in FIG. 1, the cartridge 10 may be sized to receive any number of test strips, depending on the particular application, the amount of sample available, or the like.

Figure 2:
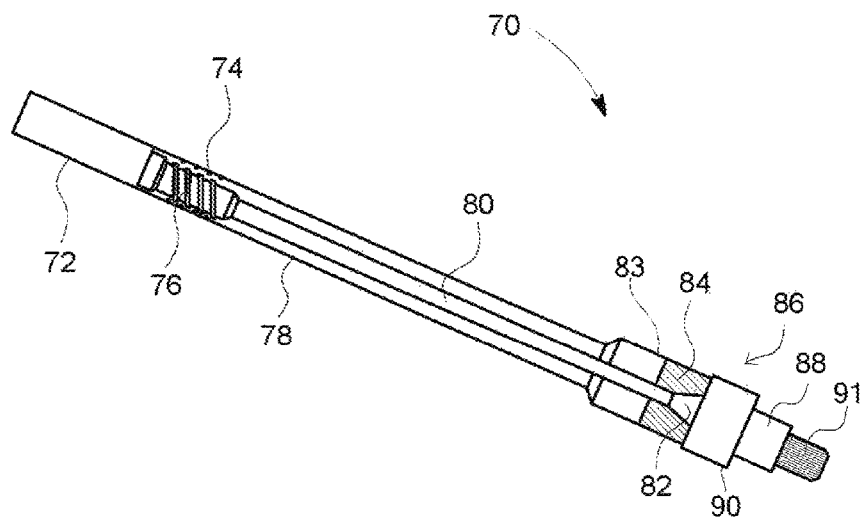
FIG. 2 illustrates a perspective view of an applicator useful in a two-step diagnostic test device according to an exemplary embodiment of the present invention.

FIG. 2 illustrates an applicator 70 that may be used to collect a specimen. The applicator 70 can include a swab 82 attached to an elongated shaft 80 having handle 72 opposite the swab 82. The shaft 80 may be a flexible shaft that permits the swab 82 to reach with a sample region, such as in a person's nose or throat, for example. As discussed in greater detail below, the male threads 76 may be formed in a region where the handle 72 and shaft 80 meet. The male threads 76 may align with female threads 74 formed on an open end of a swab receiving chamber 78. A sample releasing fluid 84 may be disposed on an end of the chamber 78, where, when the swab 82 is inserted into the chamber 78, the swab 82 is surrounded by the fluid 84. The fluid containing end 86 of the applicator 70 is connected with a narrowed region 88 which can be provided by a cap 90 to help release sample from the swab 82, as discussed in greater detail below. A cap 90 may be connected between end 86 from chamber 78 and a lid 91. A narrowed region 88 in the cap 90 may be used to release the sample when the swab 82 reaches region and rubs slightly on the periphery of region 88 when at least about three turns provided by the male thread 76 and female thread 74 are threaded together. The lid 91 can be used to close a second opening end of cap 90. The applicator 70 may be useful where sample cannot be directly applied to a sample collection pad, such as samples taken from a person's nose or throat, for example.

Figure 3:
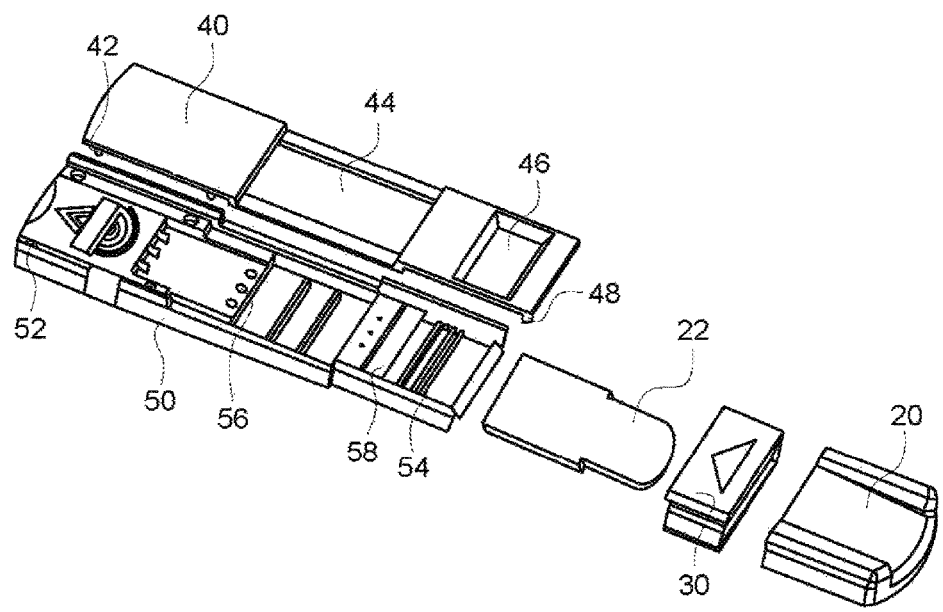
FIG. 3 illustrates an exploded of the diagnostic test device of FIG. 1.

Referring now to FIG. 3, an exploded view of the cartridge 10 is shown according to an exemplary embodiment of the present invention. An internal cavity may be formed between the top portion 40 and bottom portion 50 when assembled together where test strips may be disposed as shown in FIG. 1. Pins 42, extending from the top portion 40, may be received by pin holes 52 formed in the lower portion 50. The pins 42 and pin holes 52 may be disposed on a distal end of the cartridge 10 (distal relative to the end on which the cap 20 fits). Thus, a proximate end of the top portion 40 may function in a cantilever fashion as discussed below.

A reading window 44 may be formed in the top portion 40 to permit reading of the test strips (not shown). Test strips may be read in various methods known in the art, including by visual inspection or by electronic means. In some embodiments, the bottom portion 50 that is opposite the reading window 40 may be made of a transparent material to provide access for certain types of electronic test strip interpretation. In some embodiments, the top portion 40, including the reading window 44, may be formed from a transparent material.

A snipping knife 48 may be formed on a proximate end (proximate relative to the end on which the cap 20 fits) of the top portion 40 of the cartridge 10. As discussed below, the snipping knife 48 may be bent downward toward the bottom portion 50 as the cap 20 is slid onto the end of the cartridge 10.

A flexible pad 22, also referred to as a sample pad 22 or sample collection pad 22, may be formed in various sizes and shapes, depending on the particular application. Specimen may be received on the sample pad 22 as described in greater detail below.

Figure 5:
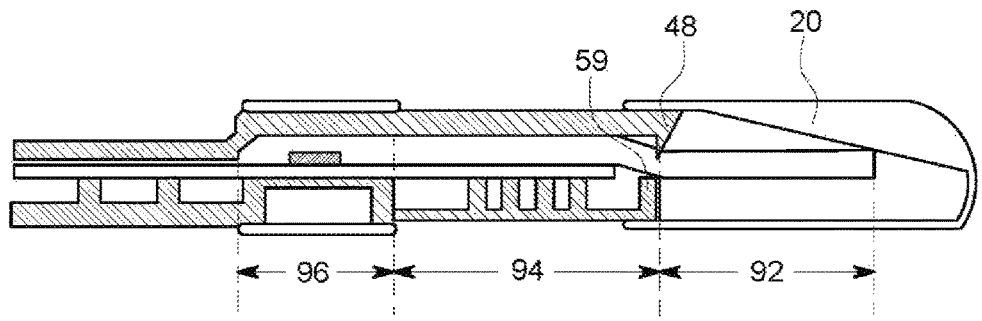
FIG. 5 illustrates a partial cross-sectional view of the diagnostic test device of FIG. 1, illustrating advancement of the cap, causing a snipping knife to approach the flexible pad.

The ring 30 may surround the outer periphery of the top portion 40 and bottom portion 50, when assembled together, and can exert a certain pressure on the second zone 94 and the third zone 96 of the sample pad 22, as described below with respect to FIG. 5.

Auxiliary supports 54, 58 may be disposed on the bottom portion 50 to support the test strips. In some embodiments, support 58 may be disposed in a region of the conjugate pad 62 (see FIG. 4) of the test strip. Test strip guides 56 may extend from the bottom portion 50 and may be used to support the test strips and keep them from overlapping each other.

The cap 20 can include an internal ramp to provide progressive compression force to one free-end cantilever of the top portion 40, which can bend down gradually to accelerate specimen flow and cut off the first zone 92 of the sample pad 22.

Figure 4:
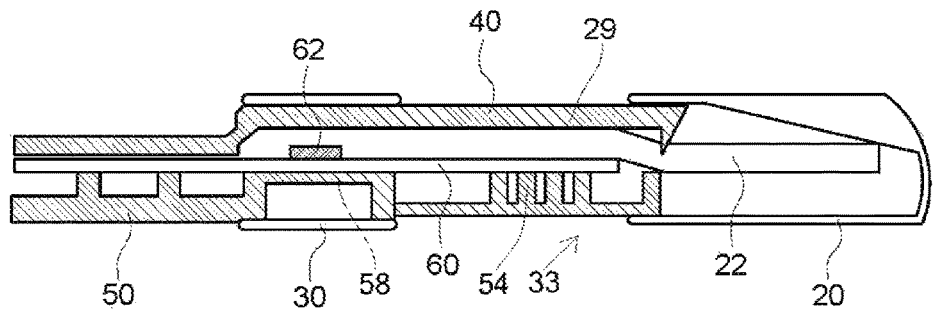
FIG. 4 illustrates a partial cross-sectional view of the diagnostic test device of FIG. 1, illustrating an initial position after sample is introduced on the flexible pad.

In some embodiments, the top portion 40 can include a sample window 46 which permits sample to be delivered onto the sample pad 22 directly inside the cartridge 10. The sample window 46, as discussed below, may be useful when used with the applicator 70 for samples that contain biological substances mixed with liquid 84. The cartridge 10 may be formed with sample window 46 (as shown in FIG. 3) as a one-step device, or without sample window 46 (as shown in FIG. 4, for example) as a two-step device, depending on specific application. The below describes a one-step method without the sample window 46, as shown in FIG. 3, which may be used on the one-step device described in FIGS. 4 through 7.

Referring now to FIGS. 4 through 7, operation of a progressive compression driven flow cartridge in a one-step device is described. The cartridge 10 can include its four main components, the top portion 40, the bottom portion 50, the cap 20, the ring 30 and the sample pad 22 integrated into a single device. The cartridge may provide a driven flow in a manner similar to U.S. Pat. Nos. 9,377,457; 9,535,061; 9,702,872; and 9,784,733, the contents of which are herein incorporated by reference. The driven flow can be provided by a cantilever or compression parts over the conjugate pad 62 of the test strip to generate a progressive driven force when coupled with the cap 20 during pushing of the cap 20 onto the body of the cartridge.

Embodiments of the present invention include a flexible pad 22 that can act not only as the sample collection pad, but also as a compression pad. The flexible pad 22 can be disposed between the conjugate pad 62 of the test strip and the cantilever deflectable end 29 of the top portion 40 to enhance the driven flow force, particularly when the specimen has a high viscosity.

Figure 6:
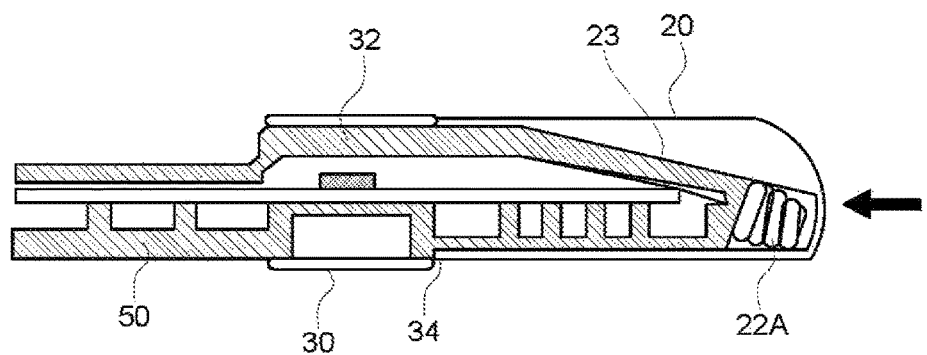
FIG. 6 illustrates a partial cross-sectional view of the diagnostic test device of FIG. 1, illustrating full advancement of the cap, where a portion of the flexible pad separated from the remainder of the flexible pad and is retained within the cap.

The flexible pad 22 can be disposed in three zones 92, 94, 96. The first zone 92 can take the role of collecting and absorbing body fluids, such as oral fluid, and then transfer the specimen to the second zone 94 and the third zone 96, which acts as a compression pad for driven flow force. After testing, if the result is positive, a further laboratory analysis for confirmation sometimes need extra authentic specimen. Therefore, the first zone 92 can be cut off by the snipping knife 48 provided from the top portion 40 that meets with a snipping foundation support 59 in the bottom portion 50, when the cap 20 is pushed onto the end of the cartridge as shown in FIGS. 5 and 6. During running of the test, after specimen has been transferred to the compression zone (the third zone 96), the cap 20 can retain the first zone 92 of the flexible pad 22 compressed into a ruffle form 22A with authentic specimen. If the text result is positive and further laboratory confirmation analysis is needed, the cap 20 can be removed from the cartridge and sealed without extra steps needed to collect specimen which could result in contamination. The simultaneous bifunctional mechanism simplifies specimen collection and testing procedures for users, particularly in some oral fluid which is not easy to collect and varies its property from time to time. The device also makes sure that the specimen left in the first zone 92, after being cut by the snipping knife 48, is authentic as the testing specimen.

Figure 7:
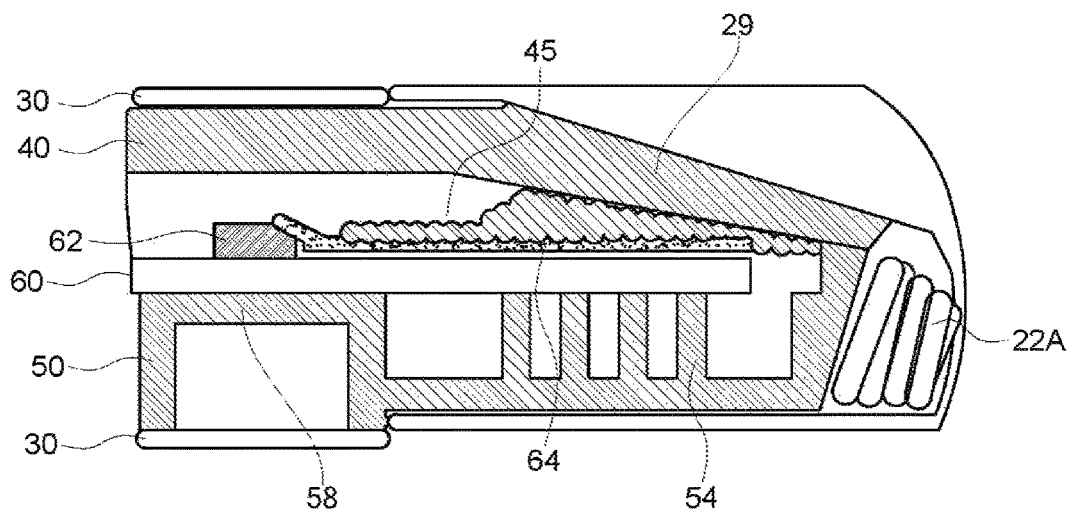
FIG. 7 illustrates a partial cross-sectional view of the diagnostic test device of FIG. 1, illustrating advancement of specimen flow toward the conjugate pad of a test strip.

As shown in FIG. 6, as the cap 20 is fully inserted onto the cartridge 10, such that end 34 of the cap 20 is adjacent the ring 30, an internal ramp 23 inside the cap 20 depresses the top portion 40 toward the bottom portion 50 to provide progressive flow of specimen 45 as illustrated in FIG. 7 along the sample pad 64, which is pre-assembled on a backing card 60 of the test strip. The separated ruffle form 22A, squeezed from the first zone 92 of the flexible pad 22, can be retained in the cap 20 while the specimen 45 continues to flow through the conjugate pad 62 which is partially attached under the sample pad 64.

In order to create the progressive specimen flow through the whole flexible pad 22, the ring 30 can be used to secure the third zone 96 of the flexible pad 22. Auxiliary supports 54 can be located under the backing card 60 of the test strip as a foundation to receive compression force from the sample pad 64. During the collection period, certain pressure exerted from the ring 30 can be applied on the second zone 94 by the top portion 40. This can drive and transfer the specimen from the second zone 94 to the sample pad 64 (which may be pre-assembled on the top of the test strip's backing card 60), which can later migrate the specimen through the conjugate pad 62 by progressive driven flow force with capillary force at the same time. When the cap 20 is pushed back to close the receiving end 34, the ramp 23 inside the cap 20 forces the cantilever deflectable end 29 of the top portion 40 to bend and pushes the specimen flow progressively faster through the conjugate pad 62. As a result, an oral fluid test can finish within about 3 minutes, which is at least three times faster than traditional lateral flow devices.

Figure 8:
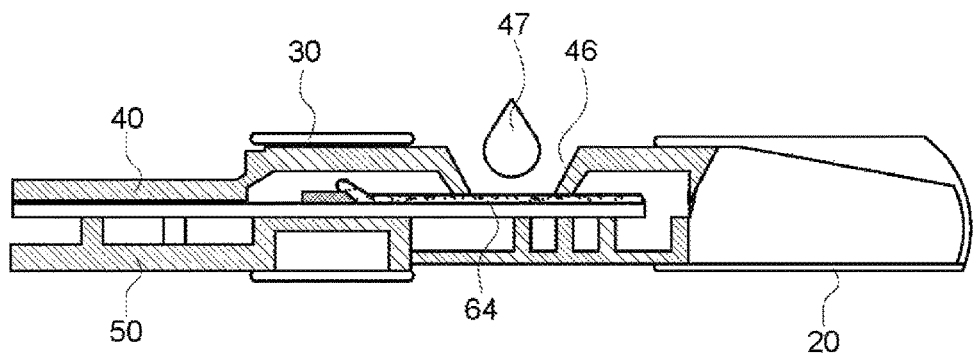
FIG. 8 illustrates a partial cross-sectional view of an alternate sample collection method, where a specimen is disposed on the flexible pad through a sample window in the diagnostic test device.

In some embodiments, as shown in FIG. 8, a sample 47 may be disposed within sample window 46 formed in the top portion 40. The sample window 46 can permit specimen 47 to be delivered directly to the sample pad 64. In this embodiment, the first zone 92 and second zone 94 of the sample pad 22 (as shown in FIG. 5) are not needed to collect and transfer specimen, as described above. The third zone 96 is used to act as a compression pad to generate drive flow force. In this embodiment, the cantilever middle deflectable section 32 can still press against the conjugate pad 62 as the cap 20 is pushed onto the end 33 of the cartridge, creating a progressive driven flow force similar to that shown in FIG. 7, for example.

The sample well formed by the sample window 46 can have a certain depth to attach its bottom onto the sample pad 64. Once the specimen 47 is dropped directly onto the pad sample 64, it is well-confined by the peripheral of the sample well and does not diffuse to other places, thereby eliminating the need for excess specimen to run the test. Therefore, on drop, or approximately 46 microliters per test strip may be enough to complete a test.

Figure 9:
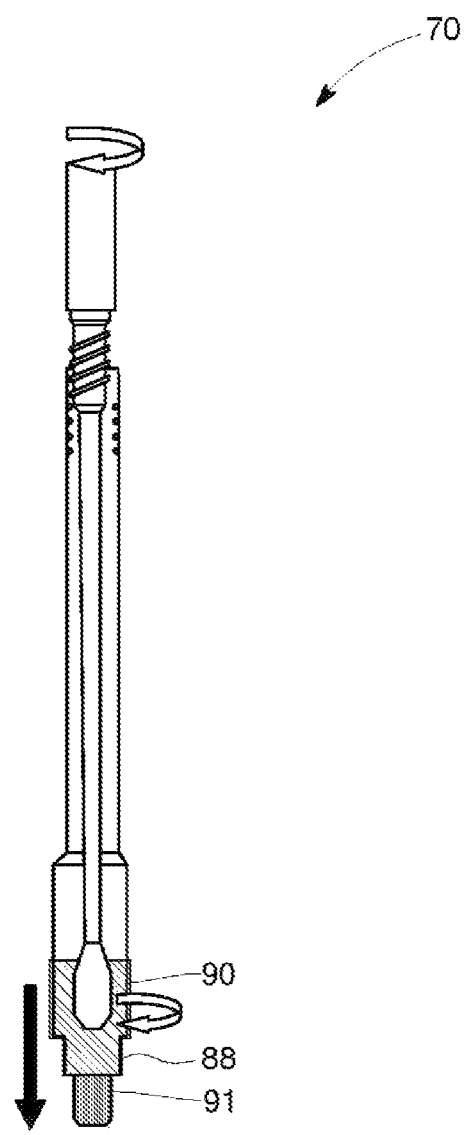
FIG. 9 illustrates a partially cut-away side view of the applicator of FIG. 2 after the swab is introduced into the chamber.
Figure 10:
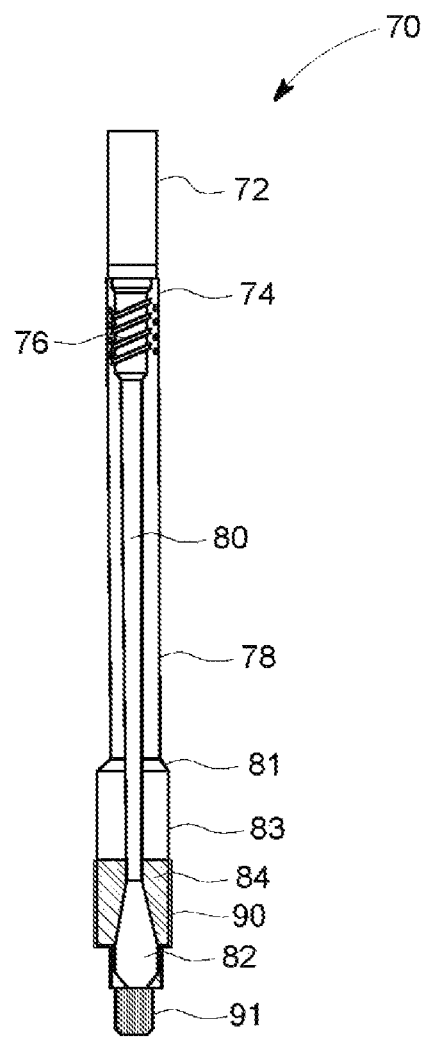
FIG. 10 illustrates a partially cut-away side view of the applicator of FIG. 2 after the sample collector is threaded into the chamber, causing advancement of the swab into a narrowed portion thereof.

The specimen 47 may be delivered via the applicator 70. Referring to FIGS. 9 and 10, the applicator 70 can include the swab 82 attached to the elongated shaft 80 having handle 72 opposite the swab 82. A narrowed ring 81 may be disposed between the receiving chamber 78 and a mixing chamber 83 to slightly rub the surface of the swab 82 to release sample from the swab 82 when the swab 82 passes through it from the receiving chamber 78 to the mixing chamber 83. The male threads 76 may be formed in a region where the handle 72 and shaft 80 meet. The male threads 76 may align with female threads 74 formed on an open end of a swab receiving chamber 78. In some embodiments, the male and female threads 76, 74 can include threads formed in about 2 to about 5 turns, typically about 3.5 turns. As the threads 76, 74 are threaded together, the swab 82 extends from the mixing chamber 82 into a narrowed region 88 of the cap 90, aiding in the release of specimen with liquid 84 from the swab 82.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A device for testing a sample for the concentration of at least one analyte, comprising:
    a test cartridge comprising:
        a base component supporting a test strip;
        a top component fitting onto the base component, sandwiching the test strip with the base component;
        a flexible pad disposed between the base component and the top component, the flexible pad positioned at least over a portion of the test strip when the test strip is disposed in the test cartridge; and
        a cap slidable over a first end of the test cartridge having the flexible pad disposed therein, the cap including an internal ramp causing the top component to be pressed toward the base component as the cap is slid onto the test cartridge; and
    a ring surrounding a portion of the base component and the top component the ring positioned to surround at least a conjugate pad portion of the test strip when the test strip is disposed in the test cartridge;
    wherein the flexible pad extends beyond the first end of the test cartridge
    further comprising a snipping knife disposed on the first end of the top component of the test cartridge, the snipping knife configured to cut the flexible pad when the cap is pressed onto the first end of the test cartridge.

2. The device of claim 1, further comprising auxiliary supports extending from the base component, the auxiliary supports positioned to support at least a portion of the test strip when the test strip is disposed in the test cartridge.

3. The device of claim 2, wherein the auxiliary supports include a support positioned below a conjugate pad of the test strip when the test strip is disposed in the test cartridge.

4. The device of claim 1, wherein the test cartridge further comprises a reading window in the top component, the reading window providing visual access of a portion of the test strip when the test strip is disposed in the test cartridge.

5. The device of claim 1, wherein an external cut portion of the flexible pad is retained inside the cap after being cut by the snipping knife.

6. The device of claim 1, wherein the test cartridge further comprises a sample well formed as an opening in the top component for placement of the sample on a sample pad of the test strip when the test strip is disposed inside the cartridge.

7. A kit comprising the device of claim 6 and an applicator for delivering the sample.

8. The kit of claim 7, wherein the applicator comprises:
    a swab attached to a first end of an elongated shaft;
    a handle attached to a second end of the elongated shaft;
    male threads formed in a region where the handle meets the elongated shaft;
    female threads, configured to mate with the male threads, formed on an open end of a swab receiving chamber;
    a sample releasing region disposed on an end of the chamber, wherein, when the swab is inserted into the chamber, the swab is received in the sample releasing region;
    a narrowed region contiguous with and extending from the sample releasing region, wherein when the male threads are threaded into the female threads, the swab extends into the narrowed region, causing the swab to contact an interior of the narrowed region; and
    a lid configured to provide a fluid connection from the narrowed region to outside the chamber.

9. The device of claim 8, wherein the sample releasing region includes a sample releasing fluid configured to remove the sample from the swab, wherein as the swab contacts the narrowed region, the sample is released from the swab into the sample releasing fluid.

10. A system for testing a sample for the concentration of at least one analyte, comprising:
    one or more test strips, each comprising:
        a sample pad configured on one end of each of the one or more test strips; and
        a conjugate pad containing nanoparticle conjugate;
    a test cartridge comprising:
        a base component supporting each of the one or more test strips next to each other;
        a top component fitting onto the base component, sandwiching each of the one or more test strips with the base component;
        a flexible pad disposed between the base component and the top component, the flexible pad positioned at least over a portion of the test strip;
        a cap slidable over a first end of the test cartridge having the flexible pad disposed therein to trigger initiation of the testing, the cap including an internal ramp causing the top component to be pressed toward the base component as the cap is slid onto the test cartridge; and a snipping knife disposed on the first end of the top component of the test cartridge, the snipping knife configured to cut a portion of the flexible pad that extends beyond the test cartridge simultaneously with the cap triggering initiation of the testing when the cap is pressed onto the first end of the test cartridge.

11. The system of claim 10, further comprising a ring surrounding a portion of the base component and the top component, the ring positioned to surround at least a conjugate pad portion of the test strip when the test strip is disposed in the test cartridge.

12. The system of claim 10, wherein the flexible pad extends beyond the first end of the test cartridge.

13. The system of claim 10, wherein the test cartridge further comprises a sample well formed as an opening in the top component for placement of the sample on the sample pad of the test strip when the test strip is disposed inside the cartridge.

\* \* \* \* \*